US011441161B2

(12) United States Patent
Yacyshyn

(10) Patent No.: US 11,441,161 B2
(45) Date of Patent: Sep. 13, 2022

(54) REMOVING POLYPHENOL CONTAMINANTS FROM FEEDSTOCK-BASED POLYPHENOLS

(71) Applicant: Vincent Yacyshyn, Calgary (CA)

(72) Inventor: Vincent Yacyshyn, Calgary (CA)

(73) Assignee: Immortazyme Company Ltd., Alberta (CA)

( * ) Notice: Subject to any disclaimer, the term of this patent is extended or adjusted under 35 U.S.C. 154(b) by 90 days.

(21) Appl. No.: 16/631,190

(22) PCT Filed: Jul. 26, 2018

(86) PCT No.: PCT/CA2018/050906
§ 371 (c)(1),
(2) Date: Jan. 15, 2020

(87) PCT Pub. No.: WO2019/018937
PCT Pub. Date: Jan. 31, 2019

(65) Prior Publication Data
US 2020/0216866 A1    Jul. 9, 2020

Related U.S. Application Data

(60) Provisional application No. 62/537,298, filed on Jul. 26, 2017.

(51) Int. Cl.
*C12P 7/625* (2022.01)
*C12P 7/64* (2022.01)

(52) U.S. Cl.
CPC ............ *C12P 7/625* (2013.01); *C12P 7/64* (2013.01)

(58) Field of Classification Search
CPC ..... C12P 7/625; C12P 7/64; C12P 7/10; C12P 19/02; C12P 7/649; C12P 7/22; Y02E 50/10
See application file for complete search history.

(56) References Cited

U.S. PATENT DOCUMENTS

| | | | |
|---|---|---|---|
| 4,126,707 A | 11/1978 | Hart | |
| 4,485,016 A | 11/1984 | Hopkins | |
| 5,871,794 A | 2/1999 | Brito | |
| 6,537,546 B2 | 3/2003 | Echigo | |
| 6,900,241 B2 | 5/2005 | Romanczyk | |
| 7,145,031 B1 | 12/2006 | Arcangeli | |
| 7,312,056 B2 | 12/2007 | Saville | |
| 7,387,802 B2 | 6/2008 | Sambanthamurthi | |
| 7,892,805 B2 | 2/2011 | Saville | |
| 8,242,130 B2 | 8/2012 | Wong | |
| 8,349,591 B2 | 1/2013 | Desbarats | |
| 8,470,380 B2 | 6/2013 | Wood | |
| 8,741,855 B2 | 6/2014 | Quave | |
| 8,771,764 B2 | 7/2014 | Abeywardena | |
| 8,818,737 B2 | 8/2014 | Yang | |
| 9,125,903 B2 | 9/2015 | Koverech | |
| 9,254,280 B2 | 2/2016 | Cole | |
| 9,283,203 B2 | 3/2016 | French | |
| 9,580,735 B2 | 2/2017 | Fukuura | |
| 9,688,712 B2 | 6/2017 | Yamada | |
| 9,743,679 B2 | 8/2017 | Perez | |
| 9,750,782 B2 | 9/2017 | Abeywardena | |
| 10,071,912 B2 | 9/2018 | Schulte | |
| 10,358,669 B2 * | 7/2019 | Desbarats | ............... C12P 7/06 |
| 2009/0311397 A1 | 12/2009 | Whalen | |
| 2010/0028484 A1 * | 2/2010 | Kriesler | ............... C12P 7/6481 |
| | | | 426/7 |
| 2013/0118590 A1 | 5/2013 | Desbarats | |
| 2016/0298155 A1 | 10/2016 | Desbarats | |
| 2017/0107452 A1 | 3/2017 | Dasari | |
| 2017/0247721 A1 | 8/2017 | Desbarats | |

FOREIGN PATENT DOCUMENTS

| | | |
|---|---|---|
| EP | 221959 | 5/1987 |
| WO | 1986/06589 | 11/1986 |
| WO | 2006/113700 | 10/2006 |
| WO | 2010/045168 | 4/2010 |
| WO | 2013/000088 | 1/2013 |

(Continued)

OTHER PUBLICATIONS

International Search Report and Written Opinion issued in PCT/CA2018/050906, dated Oct. 5, 2018, pp. 1-7.
Myburgh, "Polyphenol Supplementation: Benefits for Exercise Performance or Oxidative Stress?" Sports Med (2014) 44 (Suppl 1): S57-S70.
Tejirian, "Inhibition of enzymatic cellulolysis by phenolic compounds", Enzyme Microb Technol. Mar. 7, 2011, 48(3):239-47.
International Search Report issued in PCT/CA2018/050906, dated Oct. 1, 2018, pp. 1-3.
Datta S. et al. Biotech. Feb. 2013;3(1):1-9.
Mukai C. et al. Chem Biol. Sep. 25, 2009: 16(9): 1013-1020.

(Continued)

*Primary Examiner* — Iqbal H Chowdhury
(74) *Attorney, Agent, or Firm* — Jeffrey S. Melcher; Melcher Patent Law PLLC

(57) ABSTRACT

Provided is a method of producing a mixture of pure feedstock-based native polyphenols from a feedstock. Contaminant polyphenols are first removed from an enzyme solution for converting feedstock to a product to produce a polyphenol reduced enzyme solution. The polyphenol reduced enzyme solution is combined with the feedstock and the feedstock is converted to a product and by-product. Heretofore, there has been no process available to reduce or remove the contaminant phenols introduced to the feedstock by commercial enzyme solutions. This method allows for the removal of contaminant phenols prior to introduction to the processing stream and subsequent harvesting of pure feedstock 6 based native polyphenols. The pure feedstock-based polyphenols are removed from the product or by-product to produce a pure mixture of feedstock-based polyphenols.

9 Claims, 2 Drawing Sheets

(56) References Cited

FOREIGN PATENT DOCUMENTS

| WO | 2015/066797 | 5/2015 |
|---|---|---|
| WO | 2016/033680 | 3/2016 |
| WO | 2020/045168 | 3/2020 |

OTHER PUBLICATIONS

Ay S.S. et al. International Journal of Scientific and Technological Research vol. 4, No. 6 (2018).
Palazzo G. et al. Sensors and Actuators vol. 202,Oct. 31, 2014, pager 217-223.
Akkaya A. et al. Journal of Molecular Catalysis. vol. 67, Issues 3-4. Dec. 2010. pp. 195-201.
Blanchette C.D. et al. Printable enzyme-embedded materials for methane to methanol conversion. Nat Commun. 2016;7: 11900.
Kerem.Z Interactions between CYP3A4 and Dietary Polyphenols Oxidative Medicine and cellular Longevity. vol. 15. Article 854015. pp. 1-15.
Tsao R. Chemistry and Biochemistry of Dietary Polyphenols. Nutrients. 2010,2. 1231-1246.
Brudzynski, K et al. Polyphenol—Protein Complexes and Their Consequences for the Redux Activity, Structure, and Function of Honey. Pol. J Food Nutr. Sci. 2015 vol. 65. No. 2 pp. 71-80.
Manach C. et al. Polyphenols: food sources and bioavailability. Am J Clin Nutr. 2004; 79; 727-47.
Scalbert A. et al. Dietary Intake and Bioavailability of Polyphenols. The Journal of Nutrition 130:2073S-2085S, 2000.
Li et al. Fish Oil: A Potent Inhibitor of Platelet Adhesiveness. Blood vol. 76, No. 5 (September 1), 1990: pp. 938-945.
Tynkkynen, T. et al. NMR protocol for determination of oxidation susceptibility of serum lipids and application of the protocol to a chocolate study. Metabolomics. Jun. 2012: 8(3); 386-398.
De Sales, P.M. et al. Alpha-Amylase Inhibitors: A Review of Raw Material and Isolated Compounds from Plant Source. J Pharm Pharmaceut Sci 15(1) 141-183, 2012.
Barrett, A. et al. Inhibition of alpha-Amylase and Glucoamylase by Tannins Extracted from Cocoa, Pomegranates, Cranberries, and Grapes. J. Agric. Food Chem. 2013; 61, 1477-1486.
Kuksis, A. et al. Composition of molecular distillates of corn oil: isolation and identification of sterol esters. J Lipid Research. vol. 1 No. 4 Jul. 1960. pp. 311-319.
Ximenes et al. 2011. Deactivation of cellulases by phenols. Enzyme and Microbial Technology, vol. 48, pp. 54-60. (Year: 2011).
Zawistoska et al. 1988. Immobilized Metal Affinity Chromatography of Wheat of aamylases. Cereal chemistry, vol. 65, No. 5 , pp. 413-416. (Year: 1988).
Written Opinion issued in PCT/CA2014/000798, dated Mar. 13, 2015, pp. 1-8.
International Search Report issued in PCT/CA2014/000798, dated Mar. 13, 2015, pp. 1-6.
Jonsson, et al. "Biconversion lignocellulose: inhibitors and detoxification," Biotech Biofuels, Jan. 28, 2013, vol. 6 (16) pp. 1-10.
Kim, et al., "Soluble inhibitors/deactivators of cellulose enzymes from lignocellulosic biomass," Enzyme Microb. Tech. 2011, vol. 48, pp. 408-415.
Yang, et al., "Enzymatic hydrolysis of cellulosic biomass," Biofuels, 2011, vol. 2(4), pp. 421-450.
Sutton, "A novozymes short report: fermentation inhibitors," Nvozymes, 2011, online, retrieved Mar. 2, 2015, http://bioenergy.novozymes.com/Documents/Ferm_SR_Inhibitors.pdf.
Yennamalli, et al., "Endogluconases: insights into thermostability for biofuel applications," Biotech. Biofuels, Sep. 27, 2013, vol. 6(136), pp. 1-9.
J Agric Food Chemistry 2013, 61, pp. 1477-1486, Barrett "Inhibition of alpha-amalyase . . . ".
J. Am Leather Chem. Assoc 2003, 98, pp. 273-278.
Kulkarni et al., International Journal of Scientific and Research Publications, vol. 3, Issue 4, Apr. 2013.
Howell, "A-type cranberry proanthocyanidins and uropthogenic bacterial anti-adhesion activity," Phytochemistry, 66, pp. 2281-2291.
Ximenes et al.: 'Lignocellulose pretreatment: Beneficial and non-beneficial effects prior to enzyme hydrolysis' [ online], American Chemical Society Meeting Paper, San Diego, Mar. 25, 2012, Retrieved from the Internet: <http://www.purdue.edu/lorre/presentations/Eduardo%20ACS %203 .25 .12 .pdf.
International Search Report issued in PCT/CA2015/000482, dated Dec. 21, 2015, pp. 1-2. Attached to WO2016/033680.
International Search Report issued in PCT/CA2015/000482, dated Dec. 21, 2015, pp. 1-3.
Written Opinion issued in PCT/CA2015/000482, dated Dec. 21, 2015, pp. 1-6.

* cited by examiner

REMOVING POLYPHENOL CONTAMINANTS FROM FEEDSTOCK-BASED POLYPHENOLS

FIELD OF THE INVENTION

The invention relates to a method for producing a pure or purified mixture of native polyphenols, which native polyphenols have been harvested from an enzyme treated feedstock material.

BACKGROUND OF THE INVENTION

Polyphenols introduced during the enzymatic processing of feedstock, such as the phenols or polyphenols which are used to stabilize enzyme compositions, are impurities that foul and denature the natural, native polyphenols which are normally present in the feedstock. These impurities significantly decrease the subsequent ability to purify the native polyphenols which might be collected from grain mills, and thereby impact their subsequent value.

As described in my prior PCT patent publication No. WO 2010/045168 A1, users of industrial enzymes commonly add an entire cocktail of enzyme and polyol and metal halide salt stabilizers and other preservatives into a bioreactor, during the enzymatic treatment of a feedstock. There are a number of reasons for this, including the expense associated with separating enzymes from their metal halide salt, polymeric stabilizers and the requirement to separate enzyme from the salt, polymeric stabilizers immediately prior to addition to a bioreactor so as to minimize instability and bacterial growth. While this approach is well known, very little is known with regards to harvesting the native polyphenols which are normally present in the feedstock, once the added contaminant phenols have been removed.

As described in WO 2010/045168 A1, enzymes are often dosed at 3 locations in a grain milling plant. This includes the slurry system, where initial hydrolysis takes place, the liquefaction system, where secondary hydrolysis occurs, and the fermentation system, where final hydrolysis and fermentation of the product occurs.

While these uses of the enzyme preparation are known, WO 2010/045168 A1 does not identify the possibility of commercial enzyme modification (using similar apparatuses) with the intent of clearing or reducing the commercial enzyme inputs of their respective contaminant phenols prior to their introduction into the feedstock stream.

Surprisingly, the feedstock (including materials such as corn, wheat, barley, sorghum etc.) can include minute amounts of native polyphenols which are present in the feedstock material, and which can be collected. Moreover, these native polyphenols may be concentrated and collected in various oils from the grain processing plant after enzymatic processing. A heretofore, unrecognized benefit of the use of polyphenol reduction in the enzyme stream as outlined in my previous patents is the removal of the contaminant phenols present in commercial enzyme solutions, as stabilizers, and thereby allows for the easier and simplified capture and production of purified native polyphenols from the various feedstocks. This process provides a preferred, and industrially feasible way to separate contaminant polyphenols, which are present in the commercial enzyme solutions, from the native polyphenols present in the feedstock materials. To date, this processing ability has not been previously identified.

High purity native, or natural, polyphenols derived from the preferred feedstocks are valuable for various biologic uses including, but not limited to, their use as nutraceuticals. Reference is made to US Patent 20170107452 A1, "Dasari", paragraph [0033] which teaches that products produced from distiller's corn oil include once refined corn oil product, food grade corn oil product, and free fatty acid product which may be used in a variety of applications. The products have varying specifications for free fatty acid content and moisture content. The applications include food, feed, additives, and the manufacture of industrial products. The products include nutraceuticals as well as native polyphenols (sterols and tocopherols). However, Dasari does not disclose methods for the reduction of impurities prior to collection of the native polyphenols.

The composition of native polyphenols extracted from grain mills (wheat, corn, barley, sorghum etc.) may show beneficial human health effects. These polyphenols, once extracted in a pure manner, without contamination, are valuable for a number of applications. These effects include, but are not limited to: vasoreactivity, improved cholesterol levels, dementia clinical improvement, stroke recovery, myocardial infarction recovery, and reduction of cardiovascular death.

There are two components to polyphenol utilization. The first deals with extraction and the second with use or application With regards to polyphenol extraction, a number of prior methods exist. These include: U.S. Pat. No. 8,470,380 which teaches a method of extraction of polyphenols and claims these products as being beneficial for the treatment of cardiovascular disease, colon cancer, and digestive health; EP Patent No. 221959 B1 which describes a polyamide material useful for the removal of polyphenols from various solutions; U.S. Pat. No. 6,537,546 which teaches a process whereby phenolic compounds may be macromolecularized and prepared for various uses; and U.S. Pat. No. 4,126,707A which describes a method of grain processing whereby high protein grain husks and kernels may be separated from flour. The high protein flour is considered polyphenol rich and useful as a functional food additive. Additionally, US Patent Application 20090311397 teaches a process for edible protein extraction from corn germ. This process allows for the extraction of a liquid medium from the cereal material and the provision of a high protein content. The process entails the use of a defatted corn germ with a fat concentration of less than about 5% by weight, milling the corn germ to a granulation with a mesh of about 100 US at less than 180 degrees F. and preparing a slurry from the milled corn germ, extracting an edible protein solution from the slurry, recovering the edible protein by the use of precipitating agents (ethanol and acids) and drying the edible polyphenol rich protein.

A number of prior documents also illustrate the beneficial effects of native polyphenols. For example, U.S. Pat. No. 8,771,764 described a composition of palm oil liquor that included polyphenols and which provided improved vascular health, as measured by vascular resistance and blood pressure. U.S. Pat. No. 9,125,903 described a polyphenol rich product which included resveratrol which showed lipid lowering effects in mice. U.S. Pat. No. 8,242,130 described a combination of polyphenols including flavonoids that may be useful for the prevention and treatment of cardiovascular disease. U.S. Pat. No. 5,871,794 describes a method whereby the pulp of a tomatillo that is high in polyphenol content may be used to prevent the oxidation of guacamole. This patent is useful as the previously used sulphites that reduced o-quinones to mono or di-phenols have been banned by the US FDA. U.S. Pat. No. 6,900,241 teaches a composition for the treatment of atherosclerosis that includes polyphenols. Finally, U.S. Pat. No. 8,741,855 details a method whereby plant polyphenols may be used to prevent biofilm formation.

There are thousands of different native plant polyphenols and hundreds of these are found in edible plants and plant products. The type and content of polyphenols differs substantially between different fruit, vegetable, leaves, and seeds. Although most foods containing polyphenols have a variety of polyphenol constituents, they may be best known for the one with the highest proportion. Polyphenols are divided into family groups based on their chemical structure. There are ten or more classes of polyphenols, but the four major classes are the phenolic acids, flavinoids, stilbenes, and lignans. Each of these subclasses has hundreds of derivatives. (See Kathryn H. Myburgh. Sports Medicine 2014; 44 Suppl 1:57-70).

Further, the "polyphenol explorer database" contains 501 polyphenols with composition data classified as six classes and thirty-one sub-classes. The number of permutations and combinations of polyphenols that may be used as supplements from six categories, with thirty-one sub-groups, and approximately sixteen compounds per sub-group is over 1.8 billion. The uniqueness of finding any given combination of polyphenols that is most efficacious from the preventive human nutrition perspective will depend on the sourcing and collection of these compounds and avoidance of any chemical contamination. The extraction of various native polyphenol combinations from grain milling facilities without the introduction of phenol contaminants provides an opportunity to explore some of these unique combinations.

The complete disclosures of my previous U.S. Pat. No. 8,349,591 (Desbarats), entitled Method and apparatus for producing alcohol or sugar using a commercial-scale bioreactor, and my previous published U.S. patent application serial No. 2016-0298155 and published international application No. PCT/CA2014/000798 (Desbarats), entitled Apparatus and method for reduction of phenol in enzymatic solutions and/or feedstock, provide some background in this area, and are hereby incorporated by reference.

SUMMARY OF THE INVENTION

It is a primary object of the present invention to provide a process for removing contaminant polyphenols from commercial stabilized enzyme solutions prior to their interaction with any given feedstock such that the native polyphenols from the feedstock may be harvested in downstream processing in an uncontaminated form.

Commercial enzyme compositions contain polyphenols to stabilize the enzymes for long term storage. I have found that these polyphenols are different from the polyphenols contained in native feedstocks and may contaminate the native polyphenols which are to be subsequently extracted from the feedstock. To solve this problem, I removed the polyphenols from the enzyme solution before adding the enzyme solution to the feedstock. The result was surprisingly,—a pure feedstock-based mixture of native polyphenols essentially free of the contaminate polyphenols sourced from the enzyme composition.

Thus, in a first aspect, the present invention provides a method of producing a mixture of feedstock-based native polyphenols from a feedstock comprising a renewable biological material, comprising the steps of:

removing polyphenols from an enzyme solution for converting the feedstock to a product to produce a polyphenol reduced enzyme solution;

combining the polyphenol reduced enzyme solution with the feedstock and converting the feedstock to the product; and separating feedstock-based polyphenols from the product or a by-product of the conversion of the feedstock to the product, to produce a preferably pure mixture of feedstock-based native polyphenols free of the contaminating phenols from the enzyme solution.

In a further aspect, the present invention further includes a method of producing a mixture of feedstock-based native polyphenols from a feedstock for making alcohols or sugars, comprising the steps of:

removing polyphenols from an enzyme solution for converting feedstock to an alcohol or sugar to produce a polyphenol reduced enzyme solution;

combining the polyphenol reduced enzyme solution with the feedstock and converting the feedstock to a mixture of oil and at least one of alcohol or sugar; and separating feedstock-based polyphenols from the oil or the at least one of alcohol or sugar to produce a pure mixture of feedstock-based native polyphenols free of contaminating phenols from the enzyme solution.

BRIEF DESCRIPTION OF THE DRAWING

Embodiments of this invention will now be described by way of example only in association with the accompanying drawings in which.

DETAILED DESCRIPTION OF THE INVENTION

Figure 1:
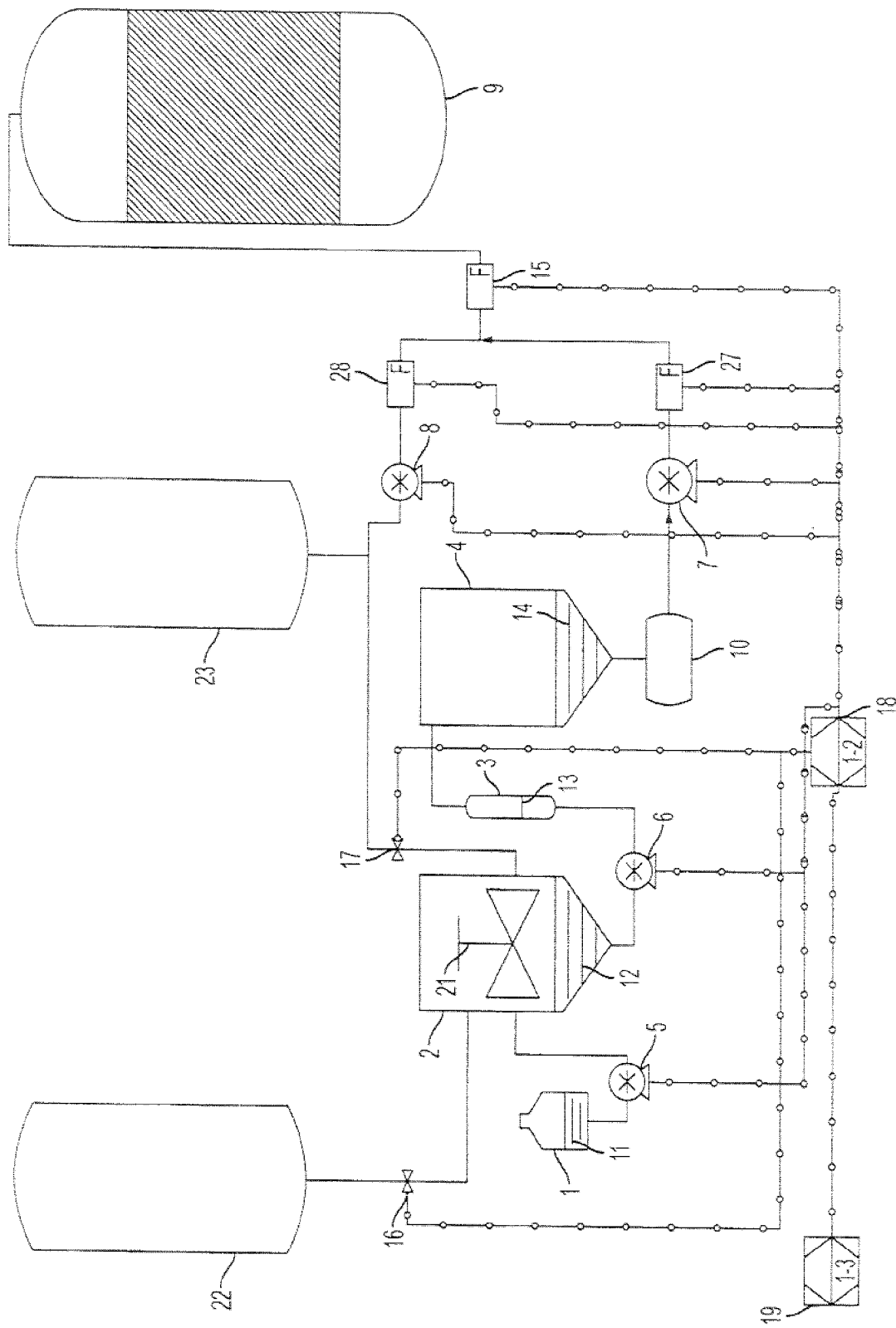
FIG. 1 shows a side view of an apparatus for reformulating stabilized enzyme preparations.

The novel features which are believed to be characteristic of the present invention, as to its structure, organization, use and method of operation, together with further objectives and advantages thereof, will be better understood from the following discussion and drawings in which a presently preferred embodiment of the invention will now be illustrated by way of example only. In the drawings, like reference numerals depict like elements.

It is expressly understood, however, that the drawings are for the purpose of illustration and description only and are not intended as a definition of the limits of the invention. Also, unless otherwise specifically noted, all of the features described herein may be combined with any of the above aspects, in any combination.

The feedstock of use in the practice of the present invention can be any renewable, biological material that can be converted to a product, such as a fuel, food or energy product, using an enzyme composition, and which contain native polyphenols. Preferred feedstocks are grain materials, such as corn, wheat, barley, sorghum, oats, rye, soybean, canola, etc. The feedstock however, can also be any carbohydrate, lipid and protein based material such as sugarcane, sugarbeets, woody biomass, grasses, algae, beans, fruits, and legumes. Preferably, the feedstock is an edible biomass.

The enzyme compositions can be any desired enzyme composition. For example, the present invention can be used in the commercial processing of feedstocks that utilize enzyme compositions, wherein the enzyme compositions comprise alpha-amylase, glucoamylase, cellulase, hemicellulase, beta-glucanase, invertase, lipase, protease, and related enzymes, or the like, to hydrolyze starch, cellulose, hemicellulose, lipids and proteins.

In general however, commercial production of products from feedstock using enzyme compositions is now well known, and the process of the present invention is applicable for any commercial production process of feedstock using enzyme compositions to make a product, and specifically when mixtures of pure feedstock-based native polyphenols are desired.

Removal of polyphenols from the enzyme composition, prior to use of the enzyme composition, can be performed using any desired process, such as, but not limited to, the process described in my previous U.S. Pat. No. 8,349,591.

Additionally, removal of the pure feedstock-based native polyphenols from the product or by-product can be achieved using any desired process for separating polyphenols from the product or by-product.

The native polyphenols from the feedstock, even those from mills used for biofuel production, can show beneficial human health effects. These effects include reduction in vasoreactivity, cholesterol levels, dementia, and cardiovascular disease including but not limited to stroke, myocardial infarction, and cardiovascular death.

The invention will now be explained with reference to the attached figures without being limited thereto.

As shown in the drawing in FIG. 1, the enzyme reformulation apparatus and method for removing contaminant phenols prior to introduction of the enzyme to the feedstock stream comprises an optional buffer vessel 1, a mixing vessel 2, a column containing a metal or metal-impregnated particulate matter or activated carbon material 3, a storage vessel 4, and an optional surge tank 10. The mixing vessel 2, the storage vessel 4, and surge vessel 10 are all preferably constructed of 304 or 316 stainless steel but can be constructed of any desired material suitable to hold the solutions.

The buffer vessel 1 contains a polymeric compound or a mixture of water and polymeric compound. The desired final concentration of polymeric compound in mixing vessel 2 can be adjusted accordingly. The polymeric compound 11 can be pumped using a variable speed pump 5 to the mixing vessel 2 containing the necessary quantity of water 22 to obtain the desired concentration of the polymeric compound. Once the final concentration of buffer is reached in mixing vessel 2, commercial enzyme preparation 23 is added to the mixing vessel 2.

Commercial enzyme preparation 23 is reformulated in the mixing vessel with water and polymeric compound. Passing the composition through the column 3 (over a time period between 1 and 15 minutes) which column is composed of a metal, a metal impregnated material, or activated carbon, facilitates the reformulation and removal of phenol contaminants in the enzyme solution, and the reformulated enzyme (and now phenol deplete solution) is collected in storage vessel 4. An optional surge tank 10 can be connected to the storage vessel 4 so that the storage vessel 4 can be emptied as desired. The reformulated and now phenol deplete enzyme solution is added to bioreactor 9. The reformulated and phenol depleted enzyme solution may sit in storage vessel 4 for up to 100 hours.

The reformulated polyphenol deplete enzyme solution can be pumped to the bioreactor with a variable speed pump 7. Two variable drive pumps 7 and 8 are in communication with each other and flow meters 27 and 28 to ensure adequate delivery of enzyme to the bioreactor.

The control system 18 for the apparatus contains programmed settings for the automated control of all valves and pumps associated with the apparatus and process. A computer screen provides visual cues to operators for tasks to complete.

Upon completion of the reformulation process for enzyme dose optimization and reduction and/or removal of phenol contaminants, the enzyme preparation is now ready for introduction to the bioreactor where the feedstock to be treated, will not be contaminated by the addition of contaminant phenols, and the reactant product(s) from the feedstock treatment, may be subsequently removed in a downstream process.

Example 1

A commercial enzyme solution was processed to decrease the amount of contaminant phenol. The reformulated, phenol reduced solution was obtained by mixing 1 part of Liquozyme SC DS, a stabilized alpha-amylase from Novozymes, with 9 parts water and 1 part propylene glycol at room temperature. The enzyme solution was passed through a column containing activated carbon over a period of 15 minutes. A 5 ml of sample was collected and subsequently analyzed.

5 ml of Liquozyme SC DS, 5 ml of reformulated, phenol reduced enzyme, and 4 grams of activated carbon were analysed by qualitative gas chromatography/mass spectroscopy (GC/MS) with a Supelco Grey (50/30 Micrometer DVB/CAR/PDMS) fiber at 80 degrees C. with 30 minute extraction time. The samples were analysed by GC/MS with water and air blanks. The sample chromatograms were evaluated against the blanks and the differences were characterized. The peaks were integrated and the average of the replicate preparations were reported.

The primary difference was the reformulated, phenol reduced enzyme contained a significant amount of propylene glycol. The Liquozyme SC DS contained more free fatty acids and sorbic acid.

At retention time 14.25 a comparison of the phenol levels was: 1,154,775 for the Liquozyme SC DS, 229,226 for diluted enzyme, 113,352 for reformulated, phenol reduced enzyme, and 69,021 for the spent activated carbon.

Figure 2:
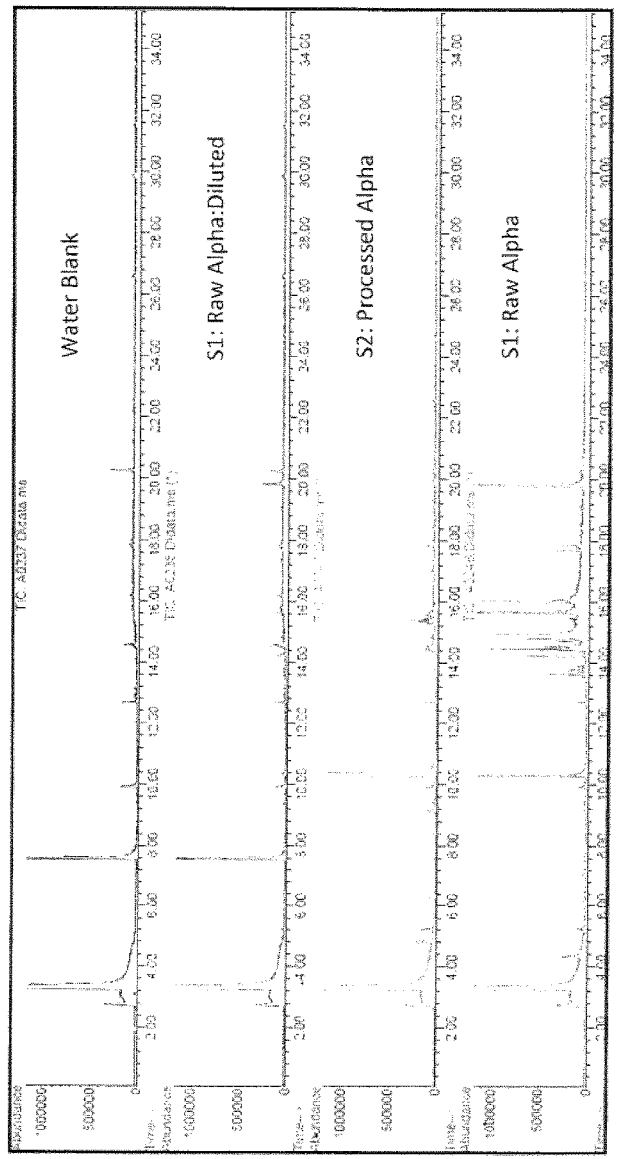
FIG. 2 is a overlaid chromatogram of various components of the present invention.

See FIG. 2 for a partial zoomed overlaid chromatogram of results.

These results illustrate the ability to reformulate a commercial enzyme and reduce phenol contamination of the subsequent enzyme product such that it may be added without activity degradation, and with phenol contamination minimized, so that the native polyphenols may subsequently be harvested from the feedstock during downstream processing.

While the claimed invention has been described in detail and with reference to specific embodiments thereof, it will be apparent to one of ordinary skill in the art that various changes and modifications can be made to the claimed invention without departing from the spirit and scope thereof.

Thus, it is apparent that there has been provided, in accordance with the present invention, a method for providing native polyphenols, and the like, which fully satisfies the goals, objects, and advantages set forth hereinbefore. Therefore, having described specific embodiments of the present invention, it will be understood that alternatives, modifications and variations thereof may be suggested to those skilled in the art, and that it is intended that the present specification embrace all such alternatives, modifications and variations as fall within the scope of the appended claims. Also, while this discussion has addressed prior art known to the inventor, it is not an admission that all art discussed is citable against the present application.

The invention claimed is:

1. A method of producing a pure mixture of native feedstock-based polyphenols from a feedstock for making alcohols or sugars, comprising the steps of:
   prior to enzymatic processing of the feedstock removing contaminating polyphenols from an enzyme solution for converting feedstock to an alcohol or sugar to produce a polyphenol removed enzyme solution;
   combining the polyphenol removed enzyme solution with the feedstock;
   enzymatic processing of the feedstock without contaminating phenols being present by converting the feedstock to at least one of alcohol or sugar, wherein contaminating polyphenols are phenols or polyphenols not sourced from the feedstock; and
   producing the pure mixture of native feedstock-based polyphenols from the feedstock free of the contaminating polyphenols from the enzyme solution by separating native feedstock-based polyphenols from at least one of the alcohol, the sugar, or a by-product of the conversion of the feedstock to the sugar or the alcohol, wherein a native composition of the feedstock-based polyphenols is preserved in the pure mixture of native feedstock-based polyphenols, and the pure mixture of native feedstock-based polyphenols free of a contaminating polyphenols is suitable for human consumption to provide a reduction of at least one of a vasoreactivity, a cholesterol level, a dementia, and a cardiovascular disease.

2. The method of claim 1, wherein the feedstock comprises a grain.

3. The method of claim 1, wherein the by-product comprises an oil.

4. A method of producing a pure mixture of native feedstock-based polyphenols from a feedstock comprising a renewable biological material, comprising the steps of:
   prior to enzymatic processing of the feedstock, removing contaminating polyphenols from an enzyme solution for converting the feedstock to a product to produce a polyphenol removed enzyme solution;
   combining the polyphenol removed enzyme solution with the feedstock;
   enzymatic processing of the feedstock without contaminating phenols being present by converting the feedstock to the product, wherein contaminating polyphenols are phenols or polyphenols not sourced from the feedstock; and
   producing the pure mixture of native feedstock-based polyphenols free of the contaminating polyphenols from the enzyme solution by separating native feedstock-based polyphenols from the product or a by-product of the conversion of the feedstock to the product, wherein a native composition of the feedstock-based polyphenols is preserved in the pure mixture of native feedstock-based polyphenols, and the pure mixture of native feedstock-based polyphenols free of a contaminating polyphenols is suitable for human consumption to provide a reduction of at least one of a vasoreactivity, a cholesterol level, a dementia, and a cardiovascular disease.

5. The method of claim 4, wherein the product comprises a biofuel, a food product or an energy product.

6. The method of claim 4, wherein the feedstock comprises a grain.

7. The method of claim 4, wherein the by-product comprises an oil.

8. The method of claim 1, wherein the cardiovascular disease includes at least one of stroke, myocardial infarction, and cardiovascular death.

9. The method of claim 4, wherein the cardiovascular disease includes at least one of stroke, myocardial infarction, and cardiovascular death.

* * * * *